US00PP10469P

United States Patent [19]

van Andel

[11] Patent Number: Plant 10,469

[45] Date of Patent: Jun. 30, 1998

[54] FREESIA PLANT VARIETY NAMED 'VARATWISNO'

[75] Inventor: Jacob van Andel, Aalsmeer, Netherlands

[73] Assignee: Van Straaveren B.V., Aalsmeer, Netherlands

[21] Appl. No.: 814,541

[22] Filed: Mar. 10, 1997

[51] Int. Cl.[6] ..... A01H 5/00

[52] U.S. Cl. ..... Plt./83

[58] Field of Search ..... Plt./83

[56] References Cited

U.S. PATENT DOCUMENTS

P.P. 487 4/1941 Bourgondien ..... Plt./83
P.P. 609 7/1943 Frazee ..... Plt./83

*Primary Examiner*—James R. Feyrer
*Assistant Examiner*—Kent L. Bell
*Attorney, Agent, or Firm*—Christie, Parker & Hale, LLP

[57] ABSTRACT

A new plant variety of freesia suitable for growing under glass as a cut flower.

1 Drawing Sheet

BACKGROUND OF THE INVENTION

This invention relates to a new and distinct variety of Freesia which originated by crossing two unpatented, unnamed varieties at the Van Staaveren Nursey in Aalsmeer, The Netherlands. The female parent is identified as 884135-AT3 and the male parent is identified as 72242H5. The varietal denomination of the new variety is 'Varatwisno'.

SUMMARY OF THE INVENTION

Among the features which distinguish the new variety from other presently available and known commercial cultivars are an attractive flower and fast flowering after planting which distinguishes 'Varatwisno' as suitable for use as a cut flower variety. Asexual reproduction of the new varety by corms and cormlets in Aalsmeer, The Netherlands has established that the distinctive characteristics are transmitted through successive generations.

Flowering Time

Under conditions of growing plants under glass in The Netherlands, Freesia plant varieties typically flower in about 22 to 23 weeks after planting for plants planted in October, about 21 to 22 weeks for plants planted in December/January; and about 20 to 30 weeks for plants planted in June/July (flowering depends on soil temperature after about 20 to 30 weeks). In contrast to the above, the flowering time after planting for 'Varatwisno' is about 19 weeks, about 18 weeks and about 17 weeks for October planting, January planting and June planting, respectively, under glass in Aalsmeer, The Netherlands.

BRIEF DESCRIPTION OF ILLUSTRATION

The accompanying photograph illustrates the new variety and shows the flowering thereof from bud to full bloom depicted in color as nearly correct as it is possible to make in a color illustration of this character. Throughout this description, color values are based upon the Colour chart of The Royal Horticultural Society of London, England, except where common terms of color definition are employed.

DESCRIPTION OF THE NEW VARIETY

The following description is of Pot Freesia Plants of the new cultivar grown under glass in Aalsmeer, Netherlands, during November. Phenotypic expression my vary with environment, cultural and climatic conditions, as well as differences and conditions in light, soil, and temperature.

Plant:

A. *Form.*—Erect.

B. *Growth.*—Height attained: Medium. Branching: No.

C. *Flower stem.*—1. Length: Medium. 2. Color: Near 143A.

D. *Foliage.*—1. Quantity: Relatively small number of leaves. 2. Size: Length—±100 cm. Width—±1.5 cm. 3. Shape of leaf: Oblongate. 4. Texture: Leaf topside — smooth; leaf underside — smooth. 5. Color: Leaf top side — near 143A. Leaf underside — near 143A. 6. Veination: Yes, normal. 7. Stem color: Near 143A. 8. Corms: Color: White with brown scales. Size: Varying.

The bud stage:

A. *Bud form.*—Long ovate.

B. *Bud size.*—About 15 mm×50 mm.

C. *Opening rate.*—Medium.

D. *Color.*—1. When petals first divide: Near 155A. 2. When petals begin to unfurl: Near 155A. 3. When flowers open: Inner Petals: Top — Near 155A; Bottom — Near 155A. Outer Petals: Top — Near 155A; Bottom — Near 155A.

E. *Calyx.*—Shape: Tubular. Size: Small.

The flower stage:

A. *Inflorescence.*—1. Blooming habit: Intermittent. 2. Form: Cup. 3. Type: Raceme. 4. Diameter: About 45mm×65 mm. 5. Approximate number of flowers: 7–9. 6. Response time from pinch: Early.

B. *Bloom.*—1. Type: Semi double-double. 2. Form: Intermittent. 3. Borne: Raceme. 4. Size (fully expanded): About 45 mm×65 mm. 5. Shape: Cup. 6. Color tonality from a distance: White. 7. Lasting quality: Long, over 14 days.

C. *Flower color.*—1. Flower coloration: White. 2. Inner petals: Near 155A. 3. Outer petals: Near 155A. 4. Point of petal attachment: Near 155A. 5. Discoloration as bloom ages: No discoloration. 6. Petals: Number of petals: 6. Arrangement: Tubular. Texture: Soft. Shape: Broad elliptic. Color: Top — Near 155A; Underside — Near 155A.

D. *Persistence.*—18 days on plant, 8 days cutting.

E. *Fragrance.*—None.

Reproductive organs:

A. *Stamens, filaments and anters.*—1. Stamens: Triple forked, white. 2. Anthers: 3 singles. Color: White with yellow base. 3. Filaments: White. 4. Pollen: White/yellow.

B. *Pistils.*—1. Styles: 3. 2. Stigmas: 1.

C. *Character of ovaries.*—Cylindrical.

D. *Calyx.*—1. Shape: Funnel. 2. Size: About 8–12 mm.

I claim:

1. A new and distinct variety of freesia plant substantially as described and illustrated herein.

* * * * *

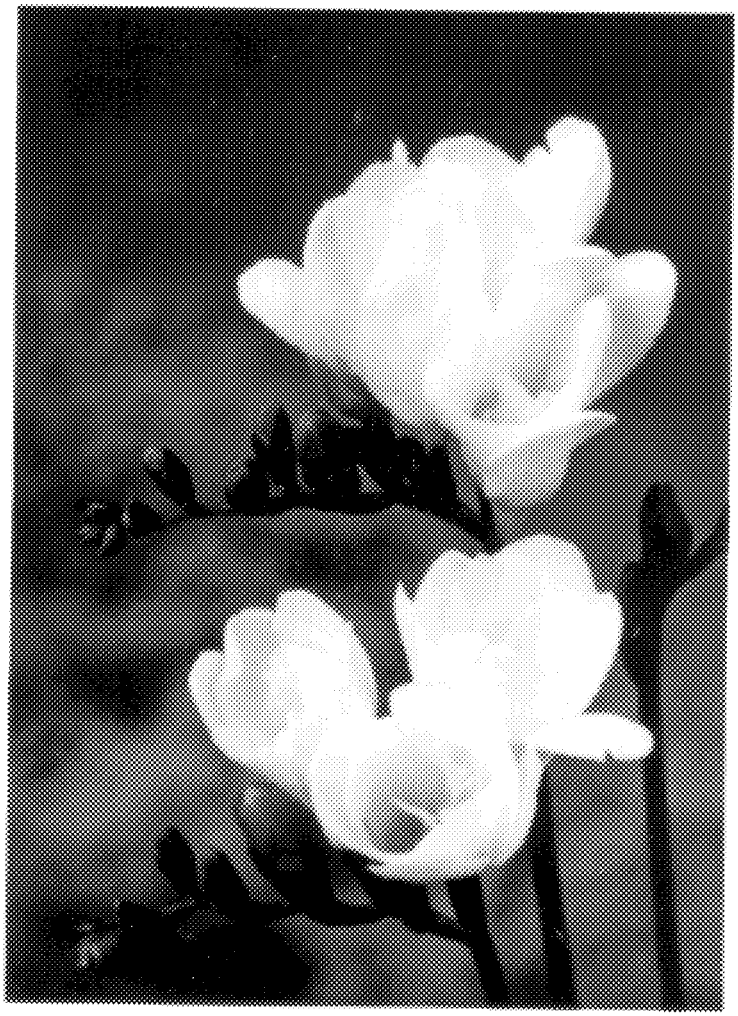

UNITED STATES PATENT AND TRADEMARK OFFICE

CERTIFICATE OF CORRECTION

PATENT NO. : Plant 10,469
DATED : June 30, 1998
INVENTOR(S) : Jacob van Andel

It is certified that error appears in the above-indentified patent and that said Letters Patent is hereby corrected as shown below:

Column 1, line 15, change "varety" to -- variety --.
Column 1, line 47, change "my vary" to -- may vary --.
Column 2, line 41, change "155A" to -- 13A --.
Column 2, line 46, before "cutting" insert -- after --.
Column 3, line 2, change "anters" to -- anthers --.

Signed and Sealed this

Fifth Day of October, 1999

*Attest:*

Q. TODD DICKINSON

*Attesting Officer*

*Acting Commissioner of Patents and Trademarks*